(12) United States Patent
Staeb et al.

(10) Patent No.: US 8,415,500 B2
(45) Date of Patent: Apr. 9, 2013

(54) ONE-STAGE REDUCTIVE AMINATION

(75) Inventors: Tobias Staeb, Frankenthal (DE); Thilo Hahn, Kirchheimbolanden (DE); Wolfgang Siegel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/808,268

(22) PCT Filed: Dec. 10, 2008

(86) PCT No.: PCT/EP2008/067192
§ 371 (c)(1),
(2), (4) Date: Jun. 15, 2010

(87) PCT Pub. No.: WO2009/080512
PCT Pub. Date: Jul. 2, 2009

(65) Prior Publication Data
US 2010/0274054 A1 Oct. 28, 2010

(30) Foreign Application Priority Data
Dec. 21, 2007 (EP) ..................... 07150298

(51) Int. Cl.
*C07C 211/27* (2006.01)
*C07C 209/62* (2006.01)

(52) U.S. Cl. ...................... 564/336; 564/471

(58) Field of Classification Search .............. 564/336, 564/471
See application file for complete search history.

(56) References Cited

FOREIGN PATENT DOCUMENTS

| DE | 44 28 004 | 2/1996 |
|---|---|---|
| DE | 198 26 396 | 12/1999 |
| EP | 0 443 606 | 8/1991 |
| EP | 1 640 358 | 3/2006 |
| WO | 2006 008171 | 1/2006 |
| WO | 2006 030017 | 3/2006 |
| WO | WO 2006030017 A1 * | 3/2006 |

OTHER PUBLICATIONS

U.S. Appl. No. 12/746,868, filed Jun. 8, 2010, Siegel, et al.

* cited by examiner

Primary Examiner — Yong Chu
(74) Attorney, Agent, or Firm — Oblon, Spivak, McClelland, Maier & Neustadt, L.L.P.

(57) ABSTRACT

A process for preparing amines of the formula I,

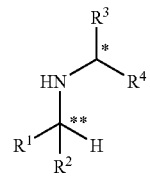

by reacting a carbonyl compound of the formula II with an amine of the formula III

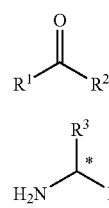
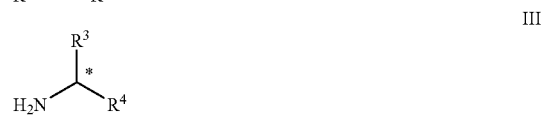

where
$R^1$ and $R^2$ are different and are each an organic radical which has from 1 to 20 carbon atoms and may optionally also comprise heteroatoms,
$R^3$ is a $C_1$-$C_6$-alkyl group and
$R^4$ is an aryl group which may be partly or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, $C_1$-$C_6$-alkylamino, di($C_1$-$C_6$-alkyl)amino, aryl and aryl($C_1$-$C_6$-alkyl); and
* represents the S or R configuration, and
** represents the S and/or R configuration;
which comprises performing the reaction in the presence of a heterogeneous imination catalyst, of a hydrogenation catalyst and of hydrogen.

19 Claims, No Drawings

ONE-STAGE REDUCTIVE AMINATION

The invention relates to a process for preparing amines of the formula I,

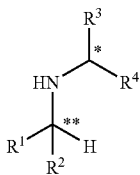

by reacting a carbonyl compound of the formula II with an amine of the formula III

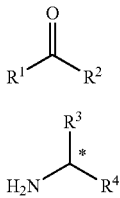

where
$R^1$ and $R^2$ are different and are each an organic radical which has from 1 to 20 carbon atoms and may optionally also comprise heteroatoms,
$R^3$ is a $C_1$-$C_6$-alkyl group and
$R^4$ is an aryl group which may be partly or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, $C_1$-$C_6$-alkylamino, di($C_1$-$C_6$-alkyl)amino, aryl and aryl($C_1$-$C_6$-alkyl); and
* represents the S or R configuration, and
** represents the S and/or R configuration;
which comprises performing the reaction in the presence of a heterogeneous imination catalyst, of a hydrogenation catalyst and of hydrogen.

Amines are important synthesis units for active ingredients in the field of pharmaceuticals and of crop protection. In the case of chiral amines (in which the substituent on the amino nitrogen bears the chirality), frequently only one stereoisomeric form (R or S form) is suitable, or, in the case of two chiral centers, only one of the diastereomeric forms (RR, RS, SR, SS).

In the preparation and reaction of amines, a high stereoselectivity or diastereoselectivity is therefore desired.

The reaction of (prochiral) ketones with chiral amines to give amino compounds which comprise two chiral centers is described, for example, in EP-A-443 606. According to the teaching of EP-A 1640 358 and WO 2006/008171, this reaction is carried out in the presence of a hydrogenation catalyst and of a Lewis acid. One disadvantage of this synthesis is the superstoichiometric and hence uneconomic use of a Lewis acid which has to be discarded after the reaction.

It was therefore an object of the present invention to provide a very simple and inexpensive process for preparing amino compounds with two chiral centers by reacting prochiral ketones with chiral amines, wherein the resulting amine should have a maximum stereoselectivity, the reaction product is easily worked up and purified and the catalyst is recyclable in a very simple manner.

Accordingly, the process defined at the outset has been found.

The Reactants

In the process according to the invention, a carbonyl compound of the formula II is reacted with an amine of the formula III.

R1 and R2 radicals in formula II (and correspondingly, of course, also in the product of the formula I) are each independently an organic radical which has from 1 to 20 carbon atoms, preferably from 1 to 10 carbon atoms, and may optionally also comprise heteroatoms. In a preferred embodiment, R1 and R2 do not comprise any heteroatoms and are each a hydrocarbon radical, especially an aliphatic hydrocarbon radical, most preferably an alkyl group.

Examples of R1 and R2 radicals include:
$C_1$-$C_6$-alkyl, $C_3$-$C_6$-cycloalkyl, $C_2$-$C_6$-alkenyl, $C_2$-$C_6$-alkynyl, $C_2$-$C_6$-haloalkenyl, $C_2$-$C_6$-haloalkynyl, $C_1$-$C_6$-alkoxycarbonyl, $C_3$-$C_6$-alkenyloxycarbonyl, $C_3$-$C_6$-alkynyloxy-carbonyl, aminocarbonyl, $C_1$-$C_6$-alkylaminocarbonyl, $C_3$-$C_6$-alkenylaminocarbonyl, $C_3$-$C_6$-alkynylaminocarbonyl, $C_1$-$C_6$-alkylsulfonylaminocarbonyl, di($C_1$-$C_6$-alkyl)aminocarbonyl, N-($C_3$-$C_6$-alkenyl)-N-($C_1$-$C_6$-alkyl)aminocarbonyl, N-($C_3$-$C_6$-alkynyl)-N-($C_1$-$C_6$-alkyl)-aminocarbonyl, N-($C_1$-$C_6$-alkoxy)-N-($C_1$-$C_6$-alkyl)-aminocarbonyl, N-($C_3$-$C_6$-alkenyl)-N-($C_1$-$C_6$-alkoxy)aminocarbonyl, N-($C_3$-$C_6$-alkynyl)-N-($C_1$-$C_6$-alkoxy)-aminocarbonyl, ($C_1$-$C_6$-alkyl)aminothiocarbonyl, di($C_1$-$C_6$-alkyl)aminothiocarbonyl and $C_1$-$C_6$-alkylcarbonyl-$C_1$-$C_6$-alkyl, where the alkyl, cycloalkyl and alkoxy radicals mentioned may be partly or fully halogenated and/or may bear from one to three of the following groups: cyano, hydroxyl, $C_1$-$C_4$-alkyl, $C_3$-$C_6$-cycloalkyl, $C_1$-$C_6$-alkoxy-$C_1$-$C_4$-alkyl, $C_1$-$C_4$-alkoxy-$C_1$-$C_4$-alkoxy-$C_1$-$C_4$-alkyl, $C_1$-$C_4$-alkoxy, $C_1$-$C_4$-alkylthio, amino, $C_1$-$C_4$-alkylamino, di($C_1$-$C_4$-alkyl)amino, $C_1$-$C_4$-alkylcarbonylamino, hydroxycarbonyl, $C_1$-$C_4$-alkoxycarbonyl, aminocarbonyl, $C_1$-$C_4$-alkylaminocarbonyl, di($C_1$-$C_4$-alkyl)aminocarbonyl or $C_1$-$C_4$-alkylcarbonyloxy;

aryl, aryl-$C_1$-$C_4$-alkyl, aryl-$C_2$-$C_4$-alkenyl, aryl-$C_2$-$C_4$-alkynyl, aryl-$C_1$-$C_4$-haloalkyl, aryl-$C_2$-$C_4$-haloalkenyl, aryl-$C_3$-$C_4$-haloalkynyl, aryl-$C_1$-$C_4$-hydroxyalkyl, arylcarbonyloxy-$C_1$-$C_4$-alkyl, aryloxycarbonyl-$C_1$-$C_4$-alkyl, aryloxy-$C_1$-$C_4$-alkyl, arylamino-$C_1$-$C_4$-alkyl, arylthio-$C_1$-$C_4$-alkyl, arylsulfinyl-$C_1$-$C_4$-alkyl, arylsulfonyl-$C_1$-$C_4$-alkyl, heterocyclyl, heterocyclyl-$C_1$-$C_4$-alkyl, heterocyclyl-$C_2$-$C_4$-alkenyl, heterocyclyl-$C_2$-$C_4$-alkynyl, heterocyclyl-$C_1$-$C_4$-haloalkyl, heterocyclyl-$C_2$-$C_4$-haloalkenyl, heterocyclyl-$C_3$-$C_4$-haloalkynyl, heterocyclyl-$C_1$-$C_4$-hydroxyalkyl, heterocyclylcarbonyloxy-$C_1$-$C_4$-alkyl, heterocyclyloxycarbonyl-$C_1$-$C_4$-alkyl, heterocyclyloxy-$C_1$-$C_4$-alkyl, heterocyclylamino-$C_1$-$C_4$-alkyl, heterocyclylthio-$C_1$-$C_4$-alkyl, heterocyclylsulfinyl-$C_1$-$C_4$-alkyl, heterocyclyl-sulfonyl-$C_1$-$C_4$-alkyl, where the aforementioned aryl and heterocyclyl radicals may be partly or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, hydroxycarbonyl-$C_1$-$C_6$-alkyl, $C_1$-$C_6$-alkoxycarbonyl-$C_1$-$C_6$-alkyl, $C_1$-$C_6$-alkoxy, $C_1$-$C_6$-haloalkoxy, hydroxycarbonyl, $C_1$-$C_6$-alkoxycarbonyl, hydroxycarbonyl-$C_1$-$C_6$-alkoxy, $C_1$-$C_6$-alkoxycarbonyl-$C_1$-$C_6$-alkoxy, amino, $C_1$-$C_6$-alkylamino, di($C_1$-$C_6$-alkyl)amino, $C_1$-$C_6$-alkylsulfonylamino, $C_1$-$C_6$-haloalkylsulfonylamino, ($C_1$-$C_6$- alkyl)aminocarbonylamino, di($C_1$-$C_6$-alkyl)amino-carbonylamino, aryl and aryl($C_1$-$C_6$-alkyl).

The $R^1$ and $R^2$ radicals are different.

In formula III (and correspondingly, of course, also in the product of the formula I), the $R^3$ and $R^4$ radicals are defined as follows:

$R^3$ is a $C_1$-$C_6$-alkyl group and $R^4$ is an aryl group which may be partly or fully halogenated and/or may bear from one to three radicals from the group of cyano, nitro, $C_1$-$C_6$-alkyl, $C_1$-$C_6$-haloalkyl, hydroxyl, $C_1$-$C_6$-hydroxyalkyl, $C_1$-$C_6$-alkoxy, $C_1$-$C_6$-haloalkoxy, hydroxycarbonyl, $C_1$-$C_6$-alkoxycarbonyl, $C_1$-$C_6$-alkylamino, di($C_1$-$C_6$-alkyl)amino, aryl and aryl($C_1$-$C_6$-alkyl).

$R^3$ is preferably a methyl group.

$R^4$ is preferably a phenyl or 1-naphthyl group.

* in formula I or III means that the compound is present either in the S configuration or alternatively in the or R configuration. It is therefore not an isomer mixture but rather a stereospecific configuration.

** in formula I represents the S and/or R configuration; i.e. the compound may be present in proportions of both configurations at this site.

The carbonyl compound II and the amine III can be used in any amounts in the reaction. If one component is used in excess, there is need to remove the unconverted amounts from the reaction mixture later; for an optimal reaction and/or for reasons of cost, it may, though, be advantageous to use one of the two components in excess.

The Catalysts

The reaction is performed in the presence of a heterogeneous imination catalyst. Imination catalysts catalyze the conversion of carbonyl compounds to the corresponding imino compounds.

The essential feature of the invention is that the imination catalyst is heterogeneous, i.e. the imination catalyst is a solid under the reaction conditions and is thus present in a different phase than the starting materials of the reaction. In contrast, homogeneous imination catalysts, as detailed by EP-A 1640358 or WO 2006/008171, are dissolved in the starting materials or in a solvent together with the starting materials, i.e. they are present in the same phase as the starting materials (homogenous catalysts).

The heterogeneous imination catalyst preferably comprises solids having a melting point of greater than 200° C. (1 bar). The imination catalyst is preferably present in the form of powder or granular material.

The heterogeneous imination catalyst preferably comprises inorganic oxides or mixed oxides.

Examples of oxides include $TiO_2$ and $ZrO_2$.

In particular, they comprise silicates or mixed oxides comprising silicon.

Silicates are particularly suitable, especially silicates which comprise further metal atoms such as aluminum, calcium, magnesium, sodium, potassium.

One example is montmorillonite. Montmorillonite generally has the composition (Na, Ca)$_{0.3}$(Al, Mg)$_2$Si$_4$(OH)$_2$ 4H$_2$O.

The imination catalyst is preferably used in amounts of from 0.1 to 20 parts by weight, more preferably from 1 to 15 parts by weight, and most preferably in amounts from 2 to 10 parts by weight, per 100 parts by weight of the total weight of the starting compounds II and III.

The reaction is also effected in the presence of a hydrogenation catalyst.

Suitable hydrogenation catalysts are all catalysts which are used for hydrogenations.

Useful active catalyst constituents include especially metals or metal oxides. These include noble metals, such as platinum, palladium, rhodium, ruthenium, and other metals such as nickel, cobalt, copper, zinc.

Suitable oxides are especially oxides of nickel, cobalt, copper, zinc.

The hydrogenation catalyst may consist solely of the active catalyst constituent; in a preferred embodiment, the active catalyst constituent is applied to an inert support (supported catalyst). The support may comprise the customary supports such as aluminum oxide, silicon oxide, titanium dioxide or calcium carbonate.

Preferred hydrogenation catalysts are, like the imination catalysts, likewise heterogeneous catalysts; particular preference is given to supported catalysts.

Particular preference is given to heterogeneous copper catalysts, especially supported copper catalysts, as hydrogenation catalysts.

The inventive reaction is therefore preferably carried out in the presence of a heterogeneous copper catalyst.

This heterogeneous copper catalyst preferably comprises, based on the total weight of the catalyst, 0.1-95% by weight of copper;

0.1-85% by weight of at least one metal selected from the group of nickel, cobalt and zinc;

0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium;

where the sum of the % by weight does not exceed 100%.

In general, the heterogeneous copper catalyst comprises a support material. Useful support materials include carbon, for example activated carbon, graphite or carbon black, or a porous metal oxide. Examples of suitable porous metal oxides are aluminum oxide, silicon dioxide, aluminosilicates, titanium dioxide, zirconium dioxide, magnesium oxide or mixtures thereof, preferably aluminum oxide, titanium dioxide and zirconium dioxide. However, it is also possible to use, as support materials, aluminum phosphate, mullite, kieselguhr, bauxite and calcium aluminate.

In particular, the total weight of the abovementioned catalytically active metals and if appropriate promoters of the heterogeneous copper catalyst, based on its total weight, is at most 95% by weight, preferably at most 90% by weight.

In one embodiment, this heterogeneous copper catalyst comprises, based on the total weight of the catalyst, 1-90% by weight of copper;

0.1-80% by weight of at least one metal selected from the group of nickel, cobalt and zinc;

0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In particular, this heterogeneous copper catalyst comprises, based on the total weight of the catalyst, 2-85% by weight of copper;

0.1-80% by weight of at least one metal selected from the group of nickel, cobalt and zinc;

0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In a further embodiment, this heterogeneous copper catalyst comprises, based on the total weight of the catalyst,
2-50% by weight of copper;
0-30% by weight of at least one metal selected from the group of nickel and cobalt;
0.5-50% by weight of zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper catalyst preferably comprises, based on the total weight of the catalyst,
5-40% by weight of copper;
0-30% by weight of at least one metal selected from the group of nickel and cobalt;
5-50% by weight of zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In particular, this heterogeneous copper catalyst comprises, based on the total weight of the catalyst,
10-35% by weight of copper;
0-30% by weight of at least one metal selected from the group of nickel and cobalt;
10-45% by weight of zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

More preferably, this heterogeneous copper catalyst comprises, based on the total weight of the catalyst,
10-35% by weight of copper;
10-40% by weight of zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In particular, this copper catalyst preferably comprises, as catalytically active metals, only copper and zinc, especially in each case (but independently) from 5 to 50% by weight, more preferably from 10 to 45% by weight, especially preferably from 20 to 40% by weight, based on the total weight of the catalyst. A useful support material is preferably a porous metal oxide, especially aluminum oxide, titanium dioxide or zirconium dioxide.

In a further embodiment, this heterogeneous copper catalyst comprises, based on the total weight of the catalyst,
2-50% by weight of copper;
0.1-70% by weight of nickel;
0-20% by weight of at least one metal selected from the group of cobalt and zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper catalyst preferably comprises, based on the total weight of the catalyst,
2-40% by weight of copper;
1-65% by weight of nickel;
0-10% by weight of at least one metal selected from the group of cobalt and zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In particular, this heterogeneous copper catalyst comprises, based on the total weight of the catalyst,
2-25% by weight of copper;
3-60% by weight of nickel;
0-10% by weight of at least one metal selected from the group of cobalt and zinc;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

More preferably, this heterogeneous copper catalyst comprises, based on the total weight of the catalyst,
2-25% by weight of copper;
3-50% by weight of nickel;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium, preferably molybdenum.

This copper catalyst preferably comprises, as catalytically active metals, only copper and nickel, especially in each case (but independently) from 2 to 15% by weight, more preferably from 2 to 10% by weight, especially preferably from 3 to 8% by weight, based on the total weight of the catalyst. A useful support material is preferably a porous metal oxide, especially aluminum oxide, titanium dioxide or zirconium dioxide. (He: example with in each case 5% by weight on $TiO_2$).

Likewise preferably, this copper catalyst comprises, as catalytically active metals or promoters, only copper, nickel and molybdenum, especially from 2 to 25% by weight of Cu, from 20 to 60% by weight of nickel, from 0.01 to 5% by weight of molybdenum, more preferably from 5 to 20% by weight of copper, from 30 to 50% by weight of nickel, from 0.1 to 2% by weight of molybdenum, especially preferably from 10 to 15% by weight of copper, from 35 to 45% by weight of nickel, from 0.5 to 1.5% by weight of molybdenum, based on the total weight of the catalyst. A useful support material is preferably a porous metal oxide, especially aluminum oxide, titanium dioxide or zirconium dioxide.

In a further embodiment, this heterogeneous copper catalyst comprises, based on the total weight of the catalyst,
2-40% by weight of copper;
0.1-80% by weight of at least one metal selected from the group of nickel and cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This heterogeneous copper catalyst preferably comprises, based on the total weight of the catalyst,
2-40% by weight of copper;
0.1-40% by weight of nickel;
0.1-40% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In particular, this heterogeneous copper catalyst comprises, based on the total weight of the catalyst,
2-30% by weight of copper;
0.5-35% by weight of nickel;
0.5-35% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

More preferably, this heterogeneous copper catalyst comprises, based on the total weight of the catalyst,
2-20% by weight of copper;
1-30% by weight of nickel;
1-30% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium, preferably molybdenum.

This copper catalyst preferably comprises, as catalytically active metals, only copper, nickel and cobalt, especially from 2 to 25% by weight of copper and in each case independently from 1 to 35% by weight of nickel and cobalt, more preferably from 2 to 20% by weight of copper and in each case independently from 10 to 30% by weight of nickel and cobalt, especially preferably from 5 to 15% by weight of copper and in each case independently from 15 to 25% by weight of nickel and cobalt, based on the total weight of the catalyst. A useful support material is preferably a porous metal oxide, especially aluminum oxide, titanium dioxide or zirconium dioxide (He: example with 11/21/21% by weight on $TiO_2$ or $ZrO_2$)

Likewise in particular, this copper catalyst comprises, as catalytically active metals, only copper, nickel and cobalt, more preferably from 2 to 10% by weight of copper and in each case independently from 1 to 10% by weight of nickel and cobalt, especially preferably from 2 to 5% by weight of copper and in each case independently from 2 to 5% by weight of nickel and cobalt, based on the total weight of the catalyst. A useful support material is preferably a porous metal oxide, especially aluminum oxide, titanium dioxide or zirconium dioxide.

In a further embodiment, this heterogeneous copper catalyst comprises, based on the total weight of the catalyst,
2-40% by weight of copper;
0.1-80% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

In particular, this heterogeneous copper catalyst comprises, based on the total weight of the catalyst,
2-20% by weight of copper;
2-20% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

More preferably, this heterogeneous copper catalyst comprises, based on the total weight of the catalyst,
2-15% by weight of copper;
2-15% by weight of cobalt;
0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

This copper catalyst preferably comprises, as catalytically active metals, only copper and cobalt, especially in each case (but independently) from 2 to 15% by weight, more preferably from 3 to 10% by weight, especially preferably from 3 to 8% by weight, based on the total weight of the catalyst. A useful support material is preferably a porous metal oxide, especially aluminum oxide, titanium dioxide or zirconium dioxide.

In a further embodiment, this heterogeneous copper catalyst comprises, based on the total weight of the catalyst,
5-40% by weight of copper;
20-80% by weight of cobalt;
0-10% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium.

More preferably, this heterogeneous copper catalyst comprises, based on the total weight of the catalyst,
10-25% by weight of copper;
40-70% by weight of cobalt;
0.1-8% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium, preferably molybdenum, manganese and phosphorus.

This copper catalyst preferably comprises, as catalytically active metals or promoters, only copper, cobalt, molybdenum and manganese, especially from 5 to 40% by weight of copper, from 30 to 80% by weight of cobalt and in each case independently from 0.1 to 10% by weight of molybdenum and manganese, more preferably from 10 to 35% by weight of copper, from 40 to 75% by weight of cobalt and in each case independently from 0.5 to 8% by weight of molybdenum and manganese, especially preferably from 12 to 25% by weight of copper, from 45 to 60% by weight of cobalt and in each case independently from 0.5 to 7% by weight of molybdenum and manganese, based on the total weight of the catalyst.

The catalyst typically has a BET surface area (determined to DIN 66131) of from 50 up to 150 $m^2/g$, preferably from 70 to 130 $m^2/g$, especially from 75 to 120 $m^2/g$. In general, the pore volume of the catalyst (determined by means of Hg porosimetry to DIN 66133) is from 0.1 to 0.4 ml/g, preferably from 0.15 to 0.35 ml/g, especially from 0.15 to 0.3 ml/g.

However, the catalyst can also be prepared by customary processes (A. Farkas, in Ullmann's Encyclopedia of Industrial Chemistry, Electronic Release 2000, Chapter 5.3, 5.4, 5.6 to 5.10).

For example, it is possible to prepare the support from corresponding compounds which are converted to the oxide of the particular support in the course of calcination. Suitable for this purpose are especially hydroxides, carbonates and carboxylates. The oxide or the corresponding precursor which is converted to the oxide of the particular support in the course of calcination can be prepared by processes known per se, for example by the sol-gel process, by precipitation, dewatering of the corresponding carboxylates, dry mixing, slurrying or spray drying. In the case of precipitation, typically soluble salts of aluminum, titanium, zirconium, etc. are used, for example the corresponding halides, preferably chloride, alkoxides, nitrate, etc., preferably nitrate of aluminum, titanium, zirconium, etc. In addition, it is possible to incorporate stabilizers into the support by customary methods. It is likewise possible to incorporate assistants which facilitate the shaping of the support, for example graphite or stearic acid, into the support. This is followed by the shaping. In general, extrudates, tablets, spheres, spall, monoliths, etc. are prepared by the customary methods.

The calcination is effected typically with air or a mixture of air and nitrogen, at a temperature of from 300 to 800° C., preferably from 500 to 600° C. It may be advantageous to add steam to the air or to the air/nitrogen mixture.

The inventive catalytically active metals or promoters can then be applied to the support. Typically, the support is impregnated with a solution of a corresponding metal precursor or promoter precursor or saturated therein. The impregnation can be effected by the incipient wetness method, in which case the porous volume of the support is filled by about the same volume of impregnation solution and—if appropriate after maturation—the support is dried; or an excess of solution is employed, in which case the volume of this solution is greater than the porous volume of the support. In this case, the support is mixed with the impregnation solution and stirred for a sufficient period. The excess impregnation solution is shaken off, centrifuged off or removed by filtration. From case to case, the addition of acids, neutral salts or bases may also facilitate the impregnation/saturation. Thorough impregnation of the support can be achieved from case to case by, for example, heating the solution during the impregnation/saturation, adding surface-active substances or evacuating the support. In addition, it is possible to spray the support with a solution of the corresponding precursor. In this case, the appropriate support is treated with a solution of the corresponding metal precursor or promoter precursor, whose properties are such that the support absorbs the solution.

However, other preparation methods known to those skilled in the art, for example chemical vapor deposition, sol impregnation, etc., are also possible.

Suitable metal precursors are corresponding soluble metal salts, including halides, especially chloride, nitrate, acetate, alkaline carbonates, formate, oxalate, citrate, tartrate.

The metal precursors or promoter precursors can be applied together or successively in the aforementioned methods. It may also be advantageous to observe a certain sequence here.

However, other preparation methods known to those skilled in the art, for example chemical vapor deposition, sol impregnation, etc., are also possible.

The support on which the inventive catalytically active metal precursors are applied is then calcined. The calcination is effected typically with air or a mixture of air and nitrogen, at a temperature of from 300 to 800° C., preferably at from 400 to 600° C. It may be advantageous to add steam to the air or to the air/nitrogen mixture.

After the calcination, the heterogeneous copper catalyst is appropriately conditioned, whether by adjusting it to a particular particle size by grinding or by grinding it and then mixing it with shaping assistants such as graphite or stearic acid, pressing it to pressings by means of a tableting press and heat treating it. The heat treatment temperatures generally correspond to the temperatures in the calcination.

However, it is also possible to prepare the heterogeneous copper catalysts by employing precipitation methods. For example, they can be prepared by a coprecipitation of the metal or promoter precursors from an aqueous salt solution comprising these metals/promoters by means of mineral bases in the presence of a slurry of a sparingly soluble oxygen-containing support precursor compound or of the support itself, and subsequent washing, drying and calcination of the precipitate obtained.

The sparingly soluble oxygen-containing support precursor compounds or supports themselves which are used may, for example, be oxides, oxyhydrates, phosphates, borates and silicates, for example oxides, oxyhydrates, phosphates, borates and silicates, for example zirconium dioxide, zirconium oxide hydrate, zirconium phosphates, borates and silicates, silicon dioxide, aluminum oxide, aluminum oxyhydrate, titanium dioxide and further compounds known to those skilled in the art. The slurries of the sparingly soluble support precursor compounds or supports themselves can be prepared by suspending fine powders of these support precursor compounds or supports themselves in water with vigorous stirring. Advantageously, these slurries are obtained by precipitating the sparingly soluble support precursor compounds from aqueous salt solutions by means of mineral bases.

In particular, the inventive heterogeneous copper catalysts are prepared via a coprecipitation of all of their components. To this end, an aqueous salt solution comprising the catalyst components is appropriately admixed under hot conditions and with stirring with an aqueous mineral base, especially an alkali metal base—for example sodium carbonate, sodium hydroxide, potassium carbonate or potassium hydroxide—until the precipitation is complete. The type of salts used is generally not critical—since the important factor in this procedure is principally the water solubility of the salts, a criterion is their good water solubility required to prepare these comparatively highly concentrated salt solutions. It is considered to be obvious that, in the selection of the salts of the individual components, of course, only salts with those anions which do not lead to disruption, whether by causing undesired precipitation or by complicating or preventing the precipitation by complex formation, are selected.

The precipitates obtained in these precipitation reactions are generally chemically inhomogeneous and consist, inter alia, of mixtures of the oxides, oxide hydrates, hydroxides, carbonates and insoluble and basic salts of the metals/promoters used. It may be found to be favorable for the filterability of the precipitates if they are aged, i.e. if they are left for a certain time after the precipitation, if appropriate under hot conditions or while passing air through.

The precipitates obtained by these precipitation processes are processed further as usual to give the inventive heterogeneous copper catalysts. After the washing, they are generally dried at from 80 to 200° C., preferably at from 100 to 150° C., and then calcined. The calcination (heat treatment) is generally performed at temperatures between 300 and 800° C., preferably at from 400 to 600° C., especially at from 450 to 550° C.

After the calcination, the heterogeneous copper catalyst is appropriately conditioned, whether by adjusting it to a particular particle size by grinding or by grinding it and then mixing it with shaping assistants such as graphite or stearic acid, pressing it to pressings by means of a tableting press and heat treating it. The heat treatment temperatures correspond generally to the temperatures in the calcination.

The heterogeneous copper catalysts prepared in this way comprise the catalytically active metals/promoters in the form of a mixture of their oxygen compounds, i.e. more particularly in the form of oxides and mixed oxides.

The heterogeneous copper catalysts prepared in this way can be stored as such.

The catalyst thus obtained can be activated before its use in the diastereoselective hydrogenation of compounds of the formula I. To this end, it is treated with hydrogen or a mixture of hydrogen and nitrogen at temperatures of from 100 to 300° C. In this context, it may be advantageous to commence with a low hydrogen content in the hydrogen/nitrogen mixture and to increase the hydrogen content continuously or stepwise in the course of the activation process. The prereduction can be carried out, for example, first at from 150 to 200° C. over a period of from 12 to 20 hours in a nitrogen/hydrogen atmosphere and then continued at from 200 to 300° C. in a hydrogen atmosphere for another up to approx. 24 hours.

The activation of the catalyst is generally carried out in the reactor in which the inventive hydrogenation is to be effected. However, it is also possible to undertake the activation of the catalyst before installation into the appropriate reactor.

Typically, the catalyst is used in the inventive hydrogenation in reduced form. In this context, it may be advantageous to activate the catalyst present in reduced form once again. To this end, it is treated with hydrogen or a mixture of hydrogen and an inert gas, for example nitrogen, at temperatures from room temperature to 100° C., preferably at from 150 to 300° C., and a hydrogen pressure of from 10 to 60 bar, preferably at max. 50 bar. In this context, it may be advantageous to activate with hydrogen without inert gas. However, it may also be advantageous to activate with a mixture of hydrogen and inert gas, in which case to begin with the hydrogen/inert gas mixture and to increase the hydrogen content continuously in the course of the activation process.

However, it is also possible to use the catalyst, in its oxidic form or else in its reduced form, in the diastereoselective hydrogenation of imines of the formula I without further preceding activation.

The Process Procedure

The reaction is effected generally in a solvent. However, it is also possible to carry out the reaction in bulk, especially when the imine of the formula I is liquid at the reaction temperature. The solvents used are solvents inert under the reaction conditions, such as alcohols, for example methanol, ethanol, n-propanol, isopropanol, cyclopentanol, cyclohexanol, ethylene glycol, propylene glycol, etc., aromatic hydrocarbons, for example benzene, toluene, ethylbenzene, xylene, etc., ethers, for example diethyl ether, methyl tert-butyl ether, ethylene glycol dimethyl ether, tetrahydrofuran, dioxane, dipolar aprotic solvents, for example N-methylpyrrolidone, dimethyl sulfoxide, sulfolane, dimethylformamide, dimethylacetamide, etc., or mixtures thereof. Preference is given to performing the reaction in an alcohol, such as methanol, ethanol, n-propanol, isopropanol, cyclopentanol, cyclohexanol, ethylene glycol, propylene glycol, etc., preferably methanol, ethanol and isopropanol or an aromatic hydrocarbon such as benzene, toluene, ethylbenzene, xylene, etc., preferably toluene or ethylbenzene, or mixtures thereof.

Typically, the reaction is performed at a temperature from room temperature to reflux temperature of the reaction mixture, generally from room temperature to 200° C., preferably from 50° C. to 150° C.

The reaction is carried out in the presence of hydrogen. The reaction can be carried out in the presence of pure hydrogen or else in the presence of a gas mixture which comprises hydrogen.

The hydrogen or the hydrogen of the hydrogen-comprising gas stream can be reacted completely or partly. In the latter case, it may be advantageous from case to case to partly or entirely recycle or circulate this gas stream. In the case that the copper catalyst used is activated before the reaction, this gas stream can also be used for this purpose.

Typically, hydrogen of technical grade quality is used. However, the hydrogen can also be used in the form of a hydrogen-comprising gas, i.e. as an addition of an inert gas, such as nitrogen, helium, neon, argon or carbon dioxide, preferably nitrogen or argon.

In general, the reaction is performed at a pressure of from 1 to 200 bar, preferably from 40 to 150 bar, especially from 50 to 100 bar. It is possible to increase the pressure up to the desired pressure stepwise or else continuously.

The process according to the invention can be carried out batchwise, semicontinuously or continuously.

In a batchwise procedure, the reaction mixture is worked up by customary methods by, for example, removing the catalyst, for example by filtration, allowing it to settle and removing the liquid phase or by centrifugation, and the solvent is removed from the filtrate, supernatant or centrifugate thus obtained, for example by distilling it off. From case to case, it may be advantageous to use a filtration aid, for example celite, if the catalyst is filtered off.

The reaction can be effected in the liquid phase, for example in a stirred autoclave, a bubble column, a circulation reactor, for instance a loop reactor or a fixed bed reactor.

A particular advantage of the process according to the invention is the recyclability of the heterogeneous imination catalyst. The catalyst can be removed after the reaction in a simple manner, for example by filtration, and reused.

The reaction time is preferably selected such that the conversion of one of the starting components is virtually complete. However, it can also be stopped earlier. Typically, the reaction is conducted for between 0.1-200 hours, preferably between 0.1-180 hours.

The reaction is preferably ended when the component present in deficiency has been converted fully. However, it may also be advantageous to end the reaction before full conversion has been attained.

A workup of the product mixture can be effected in a customary manner known to those skilled in the art; the product can be obtained, for example, by distillation, extraction or crystallization.

Preferred products of the process according to the invention are the products of the reaction of (R)- or (S)-(1-phenylethyl)amine with ethyl methyl ketone, methyl isopropyl ketone or acetophenone.

The process according to the invention is a particularly simple and inexpensive process for preparing compounds of the formula I. The number of process stages can be reduced compared to the prior art. The reaction procedure and the workup are simple. The products have a high diastereoselectivity, recognizable in the examples by a high value for the ratio of the RR/RS and SS/SR diastereoisomers.

Further Reaction

The amines of the formula I can be cleaved hydrogenolytically to give the chiral amines of the formula VIII,

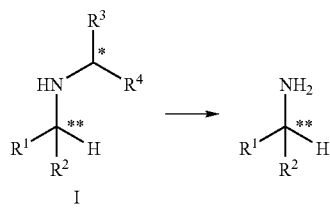

where the $R^1$, and $R^2$ radicals are each as defined for the compounds of the formula I.

This reaction can be carried out by customary and known processes.

Typically, this hydrogenolysis is carried out in an inert solvent, for example an alcohol such as methanol, ethanol, isopropanol or butanol, an ether, for example tetrahydrofuran, dioxane, a hydrocarbon, for example toluene or benzene, or mixtures thereof. The hydrogenolysis can be carried out by means of hydrogen in the presence of a catalytic amount of a platinum group metal element, preferably over Pt/C or over Pd/C. In this case, the hydrogen is generally used in excess. The reaction is effected generally at from room temperature to reflux temperature of the reaction mixture and at standard pressure up to a pressure of 200 bar. After the reaction has ended, the reaction mixture is worked up by methods known to those skilled in the art. However, it is also possible to carry out the hydrogenolysis by means of metal hydrides, for example lithium aluminum hydride, sodium boronate, sodium cyanoboronate, diborane, etc. In this case, the reactants are generally used in a stoichiometric ratio. From case to case, it may also be advantageous to use the metal hydride in excess. The reaction is effected generally at from room temperature to reflux temperature of the reaction mixture, at standard pressure. After the reaction has ended, the reaction mixture is worked up by methods known to those skilled in the art.

The hydrogenolysis of the amines of the formula II can be carried out continuously, semicontinuously or in batchwise mode.

Examples for the Patent Application

Feedstocks:

Montmorillonite K10: obtainable from Sigma-Aldrich

Pt/C. 10% Pt on carbon support

Ni/Cu/Mo analogous to DE 4428004

Ni/Co/Cu analogous to DE 19826396

Test Methods

The diastereomer ratio for examples 1-9 was determined as follows: derivatization with trifluoroacetic acid, gas chromatography separation on BGB 175 column The diastereomer ratio for examples 10-12 was determined as follows: derivatization with trifluoroacetic acid, gas chromatography separation on Hydrodex beta 6-TBDM column 1. Reaction of 2-butanone with (R)- or (S)-(1-phenylethyl)amine

EXAMPLE 1

The ketone is initially charged in a round-bottom flask with (S)-(1-phenylethyl)amine, montmorillonite K10 and Pt/C and stirred at 60° C. for 1 hour. Thereafter, hydrogen is introduced until conversion is complete.

The reaction product is a compound of the formula I where $R^1$=methyl $R^2$=ethyl $R^3$=methyl $R^4$=phenyl

TABLE 1

| Ex No. | Cat 1 | Support | Cat [g] | K10 | Ketone [g] | Amine [g] | T [° C.] | p [bar] | Run time [h] | Conversion (imine) [%] | SS/SR ratio |
|---|---|---|---|---|---|---|---|---|---|---|---|
| 1 | Pt (10) | C | 2 | 1.5 | 216 | 73 | 60 | SP | 4.5 | >99 | 66/34 |

EXAMPLES 2-9

The ketone is initially charged in an autoclave with the (R)-(1-phenylethyl)amine (table 2) or (S)-(1-phenylethyl)amine (table 3) and the two catalysts (montmorillonite K10 for the imination and a noble metal catalyst "Cat" for the hydrogenation). The apparatus is inertized with nitrogen and the mixture is stirred at the temperature specified for one hour. Hydrogen is injected thereto up to the desired pressure and hydrogenation is effected for several hours (run time). At the end, the autoclave is decompressed.

The reaction product is a compound of the formula I where $R^1$=methyl $R^2$=ethyl $R^3$=methyl $R^4$=phenyl

TABLE 2

| Ex No. | Cat 1 | Support | Cat [g] | K10 | Ketone [g] | Amine [g] | Autoclave size [ml] | T [° C.] | p [bar] | Run time [h] | Conversion (imine) [%] | RR/RS ratio |
|---|---|---|---|---|---|---|---|---|---|---|---|---|
| 2 | Ni/Cu/Mo (40/13/1) | ZrO$_2$ | 4 | 0.6 | 58 | 49 | 300 | 100 | 200 | 24 | >99 | 86/14 |
| 3 | Ni/Cu/Mo (40/13/1) | ZrO$_2$ | 1.7 | 0.5 | 50 | 42 | 300 | 100 | 70 | 24 | >99 | 86/14 |
| 4 | Ni/Co/Cu (21/21/11) | ZrO$_2$ | 1.7 | 0.5 | 50 | 42 | 300 | 100 | 70 | 24 | >99 | 85/15 |
| 5 | Pt (10) | C | 4 | 0.6 | 58 | 49 | 300 | 100 | 200 | 24 | >99 | 74/26 |

TABLE 3

| Ex No. | Cat 1 | Support | Cat [g] | K10 | Ketone [g] | Amine [g] | Autoclave size [ml] | T [° C.] | p [bar] | Run time [h] | Conversion (imine) [%] | SS/SR ratio |
|---|---|---|---|---|---|---|---|---|---|---|---|---|
| 6 | Ni/Cu/Mo (40/13/1) | $ZrO_2$ | 4 | 0.6 | 58 | 49 | 300 | 100 | 200 | 24 | >99 | 92/8 |
| 7 | Pt (10) | C | 4 | 0.6 | 58 | 49 | 300 | 100 | 200 | 24 | >99 | 74/26 |
| 8 | Ni/Cu/Mo (40/13/1) | $ZrO_2$ | 5 | 1 | 58 | 49 | 300 | 100 | 100 | 24 | 98 | 92/8 |
| 9 | Pt (10) | C | 1.9 | 0.6 | 58 | 49 | 300 | RT | 50 | 24 | >99 | 63/37 |

2. Reaction of 3-methyl-2-butanone with (R)- or (S)-(1-phenylethyl)amine

EXAMPLES 10-11

The ketone is initially charged in a round-bottom flask with (R)-(1-phenylethyl)amine (table 4) or (S)-(1-phenylethyl)amine (table 5), montmorillonite and Pt/C, and stirred at 60° C. for 1 hour. Thereafter, hydrogen is introduced until the conversion is complete. The reaction product is a compound of the formula I where
$R^1$=methyl $R^2$=isopropyl $R^3$=methyl $R^4$=phenyl

TABLE 4

| Ex No. | Cat 1 | Support | Cat [g] | K10 | Ketone [g] | Amine [g] | T [° C.] | p [bar] | Run time [h] | Conversion (imine) [%] | RR/RS ratio |
|---|---|---|---|---|---|---|---|---|---|---|---|
| 10 | Pt (10) | C | 8 | 4 | 855 | 601 | 60 | SP | 14 | >99 | 84/16 |

TABLE 5

| Ex No. | Cat 1 | Support | Cat [g] | K10 | Ketone [g] | Amine [g] | T [° C.] | p [bar] | Run time [h] | Conversion (imine) [%] | SS/SR ratio |
|---|---|---|---|---|---|---|---|---|---|---|---|
| 11 | Pt (10) | C | 4.8 | 1.5 | 172 | 121 | 60 | SP | 6 | >99 | 92/8 |

EXAMPLES 12-18

The ketone is initially charged in an autoclave with the (R)-(1-phenylethyl)amine (table 6) or (S)-(1-phenylethyl)amine (table 7) and the two catalysts (montmorillonite K10 for the imination and a noble metal catalyst "Cat" for the hydrogenation). The apparatus is inertized with nitrogen and the mixture is stirred at the temperature specified for one hour. Hydrogen is injected thereto up to the desired pressure and hydrogenation is effected for several hours (run time). At the end, the autoclave is decompressed.

The reaction product is a compound of the formula I where
$R^1$=methyl $R^2$=isopropyl $R^3$=methyl $R^4$=phenyl

TABLE 6

| Ex No. | Cat 1 | Support | Cat [g] | K10 | Ketone [g] | Amine [g] | Autoclave size [ml] | T [° C.] | p [bar] | Run time [h] | Conversion (imine) [%] | RR/RS ratio |
|---|---|---|---|---|---|---|---|---|---|---|---|---|
| 12 | Pt (10) | C | 2 | 0.6 | 50 | 35.1 | 300 | 100 | 100 | 24 | >99 | 72/28 |
| 13 | Pt (10) | C | 2 | 6 | 50 | 35.1 | 300 | 100 | 100 | 24 | >99 | 70/30 |
| 14 | Ni/Cu/Mo (40/13/1) | $ZrO_2$ | 1.4 | 0.5 | 50 | 35.2 | 300 | 100 | 70 | 24 | >99 | 96/4 |
| 15 | Ni/Co/Cu (21/21/11) | $ZrO_2$ | 1.4 | 0.5 | 50 | 35.2 | 300 | 100 | 70 | 24 | >199 | 98/2 |

TABLE 7

| Ex No. | Cat 1 | Support | Cat [g] | K10 | Ketone [g] | Amine [g] | Autoclave size [ml] | T [° C.] | p [bar] | Run time [h] | Conversion (imine) [%] | SS/SR ratio |
|---|---|---|---|---|---|---|---|---|---|---|---|---|
| 16 | Pt (10) | C | 1.9 | 0.6 | 69 | 49 | 300 | 60 | 50 | 24 | >99 | 83/17 |
| 17 | Ni/Cu/Mo (40/13/1) | ZrO$_2$ | 5 | 1 | 69 | 49 | 300 | 150 | 200 | 24 | >99 | 96/4 |
| 18 | Pt (10) | C | 1.9 | 0.6 | 69 | 49 | 300 | 60 | 50 | 24 | >99 | 82/18 |

The invention claimed is:

1. A process for preparing an amine of formula I:

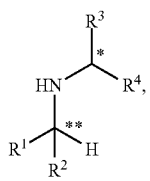

the process comprising reacting a carbonyl compound of formula II with an amine of formula III:

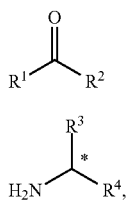

in the presence of i) a heterogeneous imination catalyst comprising a silicate or a mixed inorganic oxide comprising silicon, ii) a hydrogenation catalyst, and iii) hydrogen, to obtain an amine of formula I,
wherein:
$R^1$ and $R^2$ are different and represent an organic radical having from 1 to 20 carbon atoms and optionally comprising a heteroatom;
$R^3$ represents a $C_1$-$C_6$-alkyl group;
$R^4$ represents an aryl group which is optionally partly or fully halogenated and optionally has from one to three radicals selected from the group consisting of cyano, nitro, a $C_1$-$C_6$-alkyl, a $C_1$-$C_6$-haloalkyl, hydroxyl, a $C_1$-$C_6$-hydroxyalkyl, a $C_1$-$C_6$-alkoxy, a $C_1$-$C_6$-haloalkoxy, hydroxycarbonyl, a $C_1$-$C_6$-alkoxycarbonyl, a $C_1$-$C_6$-alkylamino, a di($C_1$-$C_6$-alkyl)-amino, an aryl and an aryl($C_1$-$C_6$-alkyl);
* represents S or R configuration; and
** represents S configuration, R configuration, or both.

2. The process according to claim 1, wherein $R^1$ and $R^2$ are different hydrocarbon radicals comprising from 1 to 20 carbon atoms.

3. The process according to claim 1, wherein $R^3$ is a methyl group.

4. The process according to claim 1, wherein $R^4$ is a phenyl or a 1-naphthyl group.

5. The process according to claim 1, wherein the hydrogenation catalyst is a heterogeneous copper catalyst.

6. The process according to claim 1, wherein the hydrogenation catalyst is a copper hydrogenation catalyst comprising from 1 to 95% by weight of copper, based on a total weight of the copper hydrogenation catalyst.

7. The process according to claim 6, wherein the copper hydrogenation catalyst is a supported catalyst.

8. The process according to claim 1, wherein the reaction occurs in the presence of a solvent or in bulk.

9. The process according to claim 1, wherein the reaction occurs at a pressure from standard pressure to 200 bar.

10. The process according to claim 1, wherein the reaction occurs at a temperature of from room temperature to a reflux temperature of the reaction mixture.

11. The process according to claim 1, wherein the reaction occurs in one stage such that any intermediates formed are not isolated.

12. A process for preparing a chiral amine of formula IV:

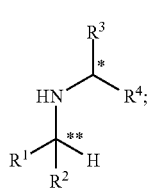

the process comprising:
a) reacting a carbonyl compound of formula II with an amine of formula III:

in the presence of i) a heterogeneous imination catalyst comprising a silicate or a mixed inorganic oxide comprising silicon, ii) a hydrogenation catalyst, and iii) hydrogen to obtain an amine of formula I:

and subsequently
b) hydrogenolytically cleaving the amine of formula I to obtain the amine of formula IV, wherein:

R$^1$ and R$^2$ are different and represent an organic radical having from 1 to 20 carbon atoms and optionally comprising a heteroatom;

R$^3$ represents a C$_1$-C$_6$-alkyl group;

R$^4$ represents an aryl group which is optionally partly or fully halogenated and optionally has from one to three radicals selected from the group consisting of cyano, nitro, a C$_1$-C$_6$-alkyl, a C$_1$-C$_6$-haloalkyl, hydroxyl, a C$_1$-C$_6$-hydroxyalkyl, a C$_1$-C$_6$-alkoxy, a C$_1$-C$_6$-haloalkoxy, hydroxycarbonyl, a C$_1$-C$_6$-alkoxycarbonyl, a C$_1$-C$_6$-alkylamino, a di(C$_1$-C$_6$-alkyl)-amino, an aryl and an aryl(C$_1$-C$_6$-alkyl);

* represents S or R configuration; and

** represents S configuration, R configuration, or both.

13. The process according to claim 2, wherein R$^3$ is a methyl group.

14. The process according to claim 1, wherein the heterogeneous imination catalyst comprises a silicate comprising at least one further metal selected from the group consisting of aluminum, calcium, magnesium, sodium and potassium.

15. The process according to claim 1, wherein the heterogeneous imination catalyst comprises a mixed oxide comprising silicon.

16. The process according to claim 1, wherein the heterogeneous imination catalyst comprises a montmorillonite.

17. The process according to claim 1, wherein the hydrogenation catalyst comprises:
- 0.1-95% by weight of copper;
- 0.1-85% by weight of at least one metal selected from the group of nickel, cobalt and zinc; and
- 0-5% by weight of at least one promoter selected from the group of iron, rhodium, ruthenium, palladium, platinum, iridium, osmium, silver, gold, molybdenum, tungsten, rhenium, cadmium, lead, manganese, tin, chromium, lithium, sodium, potassium, cesium, magnesium, barium, phosphorus, arsenic, antimony, bismuth, selenium and tellurium, wherein the sum of the % by weight does not exceed 100%, based on a total weight of the catalyst.

18. The process according to claim 17, wherein the hydrogenation catalyst comprises copper, nickel and molybdenum.

19. The process according to claim 17, wherein the hydrogenation catalyst comprises copper, nickel and cobalt.

* * * * *